(12) United States Patent
Dömling et al.

(10) Patent No.: US 7,816,377 B2
(45) Date of Patent: Oct. 19, 2010

(54) TUBULYSIN ANALOGUES

(75) Inventors: Alexander Dömling, Munich (DE); Bernd Henkel, Planegg (DE); Barbara Beck, Bethesda, MD (US); Katrin Illgen, Planegg (DE); Sukumar Sakamuri, San Diego, CA (US); Sanjay Menon, Plainsboro, NJ (US)

(73) Assignee: R&D-Biopharmaceuticals GmbH, Martinsried (DE)

( * ) Notice: Subject to any disclaimer, the term of this patent is extended or adjusted under 35 U.S.C. 154(b) by 914 days.

(21) Appl. No.: 10/520,793

(22) PCT Filed: Jul. 9, 2003

(86) PCT No.: PCT/EP03/07419

§ 371 (c)(1),
(2), (4) Date: Jul. 8, 2005

(87) PCT Pub. No.: WO2004/005327

PCT Pub. Date: Jan. 15, 2004

(65) Prior Publication Data

US 2005/0239713 A1    Oct. 27, 2005

(30) Foreign Application Priority Data

Jul. 9, 2002 (DE) ................. 102 30 874
Nov. 13, 2002 (DE) ................. 102 52 719

(51) Int. Cl.
*A61K 31/445* (2006.01)
*C07D 417/12* (2006.01)

(52) U.S. Cl. ...................... 514/326; 546/209

(58) Field of Classification Search .............. 514/326; 546/209

See application file for complete search history.

(56) References Cited

FOREIGN PATENT DOCUMENTS

DE    196 38 870    *   3/1998
DE    100 08 089    *  10/2001

OTHER PUBLICATIONS

Noren "Myxobacteria . . . " Myxobacteria . . . CA 52:93347 (1958).*
Grever et al. "The national cancer institute . . . " Seminars in Oncology, v. 19, p. 622-638 (1992).*
ATCC catalog information pp. 1-3 (2009).*

* cited by examiner

*Primary Examiner*—Celia Chang
(74) *Attorney, Agent, or Firm*—Edwards Angell Palmer & Dodge LLP; Peter F. Corless; Nicholas J. DiCeglie, Jr.

(57) ABSTRACT

The invention relates to tubulysin derivatives of general formula (II), said derivatives having a cytostatic effect.

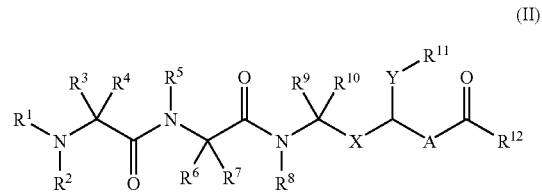

17 Claims, No Drawings

TUBULYSIN ANALOGUES

The present invention refers to novel tubulysin analogs and its use for the treatment of cancer diseases.

Tubulysins, for the first time were isolated by Höfle and Reichenbach et al. (GBF Braunschweig) from a culture growth of the myxobacterial strains of *Archangium gephyra* (F. Sasse et al. J. Antibiot. 2000, 53, 879-885; WO9813375; DE 10008089). These compounds show high cytotoxicity in the low picomolare $IC_{50}$ in a panel of cancer cell lines; thus they are of interest as potential anticancer therapeutics. Tubulysins (I) are tetrapeptides, containing three unusual amino acids; thus the total synthesis pose a considerable challenge to organic chemists.

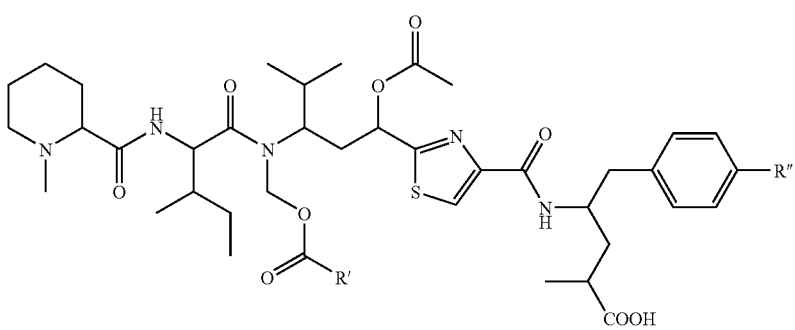

(I)

Tubulysin A: R'=CH$_2$CH(CH$_3$)$_2$; R"=OH
Tubulysin B: R'=CH$_2$CH$_2$CH$_3$; R"=OH
Tubulysin C: R'=CH$_2$CH$_3$; R"=OH
Tubulysin D: R'=CH$_2$CH(CH$_3$)$_2$; R"=H
Tubulysin E: R'=CH$_2$CH$_2$CH$_3$; R"=H
Tubulysin F: R'=CH$_2$CH$_3$; R"=H It is an objective of the present invention to provide novel Tubulysin analogues with improved activity and properties, in particular pharmacological properties as compared to the natural products.

The present invention provides a compound of Formula (II):

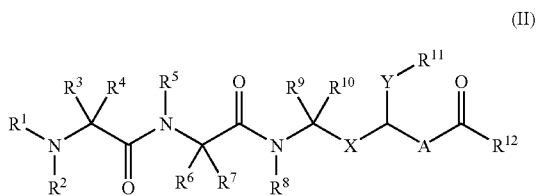

(II)

wherein
A is a substituted 5- or 6-membered heteroaryl;
wherein
X is O, S or $NR^{13}$ or $CR^{14}R^{15}$;
wherein
Y is O, S or $NR^{16}$;
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ are independently H, alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl, or two R's are members of a cycloalkyl or heterocycloalkyl ring system;
wherein compounds of Formula (I) are excluded,
wherein R' are H, alkyl, alkenyl, aryl or heteroaryl and—at the same time—R" are H, —OH, alkyl, aryl, or heteroaryl; or a pharmacologically acceptable salt, a solvate, a hydrate or a pharmacologically acceptable formulation thereof. Explicitly excluded are Tubulysins A, B, C, D, E and F.

The term alkyl or alk refers to a saturated, linear or branched hydrocarbon group, containing from one to twenty carbon atoms, preferably from one to twelve carbon atoms, mostly preferred from one to six carbon atoms, for example methyl, ethyl, propyl, isopropyl, isobutyl, n-butyl, tert-butyl, n-hexyl, 2,2-dimethylbutyl or n-octyl.

The term alkenyl and alkinyl refers to a at least partially unsaturated, linear or branched hydrocarbon group, containing from two to twenty carbon atoms, preferably from two to twelve carbon atoms, mostly preferred from two to six carbon atoms, for example ethenyl, allyl, acetylenyl, prpargyl, isoprenyl, or hex-2-enyl. Preferentially alkenyl groups contain one or two, mostly preferred one double bond and alkinyl group contain one or two, mostly preferred one triple bond.

Optionally the term akyl, alkenyl and alkinyl refers to groups where one or several, preferentially one, two or three hydrogen atoms are replaced by a halogen atom, preferentially fluorine or chlorine or a 2,2,2-trichlorethyl, or a trifluoromethyl.

The term heteroalkyl refers to a alkyl, alkenyl or alkinyl group, where several, preferentially one, two or three carbon atoms are replaced by a O, N, P, B, Se, Si, or S atom, preferentially O, S, N. The term heteroalkyl refers to a carboxylic acid or a thereof derived group, for example acyl (alkyl-CO), acylalkyl, alkoxycarbonyl, acyloxy, acyloxyalkyl, carboxyalkylamid or alkoxycarbonyloxy.

Examples of heteroalkyl groups are groups of the formula $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ refers to a H, a $C_1$-$C_6$-alkyl, a $C_2$-$C_6$-alkenyl or a $C_2$-$C_6$-alkinyl group; wherein $R^b$ refers to a H, a $C_1$-$C_6$-alkyl, a $C_2$-$C_6$-alkenyl or a $C_2$-$C_6$-alkinyl group; wherein $R^c$ refers to a H, a $C_1$-$C_6$-alkyl, a $C_2$-$C_6$-alkenyl or a $C_2$-$C_6$-alkinyl group; wherein $R^d$ refers to a H, a $C_1$-$C_6$-alkyl, a $C_2$-$C_6$-alkenyl or a $C_2$-$C_6$-alkinyl group and $Y^a$ refers to a direct binding, a $C_1$-$C_6$-alkylen, a $C_2$-$C_6$-alkenylen or a $C_2$-$C_6$-alkinylen group, wherein each heteroalkyl group can be replace by a carbon atom and one or several hydrogen atoms can be replaced by fluorine or chlorine atoms. Examples of heteroalkyl groups are methoxy, trifluormethoxy, ethoxy, n-propyloxy, iso-propyloxy, tert-butyloxy, methoxymethyl, ethoxymethyl, methoxyethyl, methylamino, ethylamino, dimethylamino, diethylamino, iso-propylethylamino, methyl-aminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxy-carbonyl, N-ethyl-N-methylcarbamoyl or N-methylcarbamoyl. Other examples of heteroalkyl groups are nitrile, isonitrile, cyanate, thiocyanate, isocyanate, isothiocyanate and alkylnitrile groups.

The term cycloalkyl refers to a saturated or partially unsaturated (e.g. cycloalkenyl) cyclic group, comprising one or several rings, preferentially one or two, containing three to fourteen ring carbon atoms, preferentially three to ten, preferentially three, four, five, six or seven ring carbon atoms. Furthermore the term cycloalkyl refers to a group where one or more hydrogen atoms are replaced by F, Cl, Br, I, OH, $=O$, SH, $=S$, $NH_2$, $=NH$, or $NO_2$, or cyclic ketones, for example cyclohexanone, 2-cyclohexenone or cyclopentanone. Examples of cycloalkyl groups are cyclopropyl, cyclobutyl, cyclopentenyl, spiro[4,5]-decanyl, norbornyl, cyclohexyl, cyclopentenyl, cyclohexadienyl, decalinyl, cubanyl, bicyclo[4.3.0]nonyl, tetralin, cyclopentylcyclohexyl, fluor-cyclohexyl or the cyclohex-2-enyl group.

The term heterocycloalkyl refers to the above definition, wherein a or several, preferentially one, two or three ring carbon atoms are replaced by a O, N, Si, Se, P, or S, preferentially O, S, N. Preferentially a heterocycloalkyl groups is composed of one or two rings comprising three to ten, preferentially three, four, five, six or seven ring atoms. Moreover the term heterocycloalkyl refers to groups where a or several hydrogen atoms are replaced by F, Cl, Br, I, OH, $=O$, SH, $=S$, $NH_2$, $NO_2$. Examples of heterocycloalkyl are piperidyl, morpholinyl, urotropinyl, pyrrolidinyl, tetrahydrothiophenyl, tetrahydropyranyl, tetrahydro-furyl, oxacyclopropyl, azacyclopropyl or 2-pyrazolinyl groups as well as lactams, lactons, cyclic imides and cyclic anhydrides.

The term alkylcycloalkyl refers to groups, which contain cycloalkyl as well as alkyl, alkenyl or alkinyl groups according to the above definition, e.g. alkylcycloalkyl, alkylcycloalkenyl, alkenylcycloalkyl and alkinylcycloalkyl groups. Preferentially a alkylcycloalkyl group is composed of a cycloalkyl group, comprising one or more rings, comprising three to ten, preferentially three, four, five, six or seven carbon—atoms and one or two alkyl, alkenyl other alkinyl groups with one or two to six carbon atoms.

The term heteroalkylcycloalkyl refers to alkylcycloalkyl groups, according to the above definition, wherein one or several, preferentially one, two or three carbon atoms are replaced by O, N, Si, Se, P or S, preferentially O, S, N. Preferentially it is composed of a heteroakylcycloalkyl group comprising one or two ring systems with three to ten, preferentially three, four, five, six or seven ring atoms and one or two alkyl, alkenyl, alkinyl or heteroalkyl groups with one or two to six carbon atoms. Examples of such a group are alkylheterocycloalkyl, alkylheterocycloalkenyl, alkenyl-heterocycloalkyl, alkinylheterocycloalkyl, heteroalkyl-cycloalkyl, heteroalkylheterocycloalkyl and heteroalkylheterocylcloalkenyl, wherein the cyclic group is saturated or partially (simply, twofold or threefold) unsaturated.

The term aryl or ar refers to a aromatic group, composed of one or several rings, comprising six to fourteen carbon atoms, preferentially six to ten, preferentially six carbon atoms. The term aryl or ar refers to a aromatic group, wherein one or several H atoms are replaced by F, Cl, Br or I or OH, SH, $NH_2$, or $NO_2$. Examples are phenyl-, naphthyl-, piphenyl-, 2-fluorphenyl, anilinyl-, 3-nitrophenyl or 4-hydroxy-phenyl.

The term heteroaryl refers to a aromatic group, composed of one or several rings, comprising five to fourteen rind atoms, preferentially five to ten, and a or several, preferentially one, two, three or four O, N, P or S ring atoms, preferentially O, S or N. The term heteroaryl refers to groups, wherein one or several H atoms are replaced by F, Cl, Br or I or OH, SH, $NH_2$, or $NO_2$. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, chinolinyl, purinyl, carbazolyl, acridinyl, pyrimidyl, 2,3'-bifuryl, 3-pyrazolyl and iso-chinolinyl.

The term aralkyl refers to groups, in accordance to the above definition, composed of aryl and alkyl, alkenyl, alkinyl and/or cycloalkyl, e.g. arylalkyl, arylalkenyl, arylalkinyl, arylcycloalkyl, arylcycloalkenyl, alkylarylacycloalkyl and alkylarylcycloalkenyl. Examples of aralkyles are toluol, xylol, mesitylen, styren, benzylchloride, o-fluortoluene, 1H-inden, tetralin, dihydronaphthaline, indanon, phenylcyclopentyl, cumol, cyclo-hexylphenyl, fluoren and indan. Preferentially, a aralkyl group is composed of composed of one or two aromatic rings, comprising six to ten ring carbon atoms and one or two alkyl, alkenyl and/or alkinyl comprising one or two to six carbon atoms and/or one cyclo-alkyl comprising five or six ring carbon atoms.

The term heteroaralkyl refers to groups, in accordance to the above definition, wherein one or several, preferentially one, two, three or four carbon atoms are replaced by O, N, Si, Se, P, B, S, preferentially O, N or S, and groups which according to the above definition contain aryl, heteroaryl and alkyl, alkenyl, alkinyl and/or heteroalkyl and/or cycloalkyl and/or heterocyclo-alkyl. Preferentially a heteroaralkyl group is composed od a or two aromatic ring systems comprising five or six to ten carbon atoms and one or two alkyl, alkenyl and/or alkinyl comprising one or two to six carbon atoms and/or one cycloalkyl comprising five or six ring carbon atoms, wherein one, two, three or four carbon atoms can be replaced by O, N or S.

Examples are arylheteroalkyl, arylheterocycloalkyl, arylheterocycloalkenyl, arylalkylheterocycloalkyl, arylalkenylheterocycloalkyl, arylalkinylheterocyclo-alkyl, arylalkylheterocycloalkenyl, heteroarylalkyl, heteroarylalkenyl, heteroarylalkinyl, heteroarylheteroalkyl, heteroarylcycloalkyl, heteroarylcycloalkenyl, heteroarylheterocycloalkyl, heteroarylheterocycloalken-yl, heteroarylalkylcycloalkyl, heteroarylalkylhetero-cycloalkenyl, heteroarylheteroalkylcycloalkyl, Hetero-arylheteroalkylcycloalkenyl and heteroarylheteroalkyl heterocycloalkyl, wherein the cyclic groups can be saturated or simple, twice, three fold of four fold unsaturated. Examples are tetrahydroisochinolinyl, benzoyl, 2- or 3-ethyl-indolyl, 4-methylpyridino, 2-, 3- or 4-methoxyphenyl, 4-ethoxyphenyl, 2-, 3- or 4-carboxyphenylalkyl.

The terms cycloalkyl, heterocycloalkyl, alkylcyclo-alkyl, heteroalkylcycloalkyl, aryl, heteroaryl, aralkyl and heteroaralkyl refer to groups, wherein one or several H atoms are replaced by F, Cl, Br or I or OH, SH, $NH_2$, or $NO_2$.

The term "optinally substituiert" relates to groups, wherein one or several H atoms are replaced by F, Cl, Br or I or OH, SH, $NH_2$, or $NO_2$. The term "gegebenenfalls substituiert" relates further to groups, comprising exclusively or in addition unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl.

Protecting groups are known to the specialist and described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999. Common amino protecting groups are e.g. t-butyloxycarbonyl (Boc), benzyloxycarbonyl (Cbz, Z), benzyl (Bn), benzoyl (Bz), fluorenylmethyloxycarbonyl (Fmoc), allyloxycarbonyl (Alloc), trichlorethyloxycarbonyl (Troc), acetyl or trifluoracetyl.

Compounds of Formula (II) can comprise several chiral centers related to their substitution pattern. The present invention relates to all al defined enantio and diastereo isomers as well as their mixtures in all ratios. Moreover the present invention relates to all cis/trans isomers of compounds of the general Formula (II) as well as their mixtures. Moreover the present invention relates to all tautomeric forms of compounds of the general Formula (II).

Preferably A constitutes a optinally substituted thizol ring; more preferably A has the following structure:

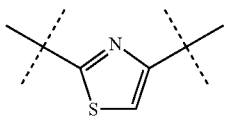

Moreover preferably X constitutes a $CH_2$ group.

Preferably Y constitutes O.

Preferably $R^1$ constitutes a $C_1$-$C_4$ alkyl.

Preferably $R^2$ ans $R^3$ constitute together $(CH_2)_n$ with n=2, 3, 4 or 5.

Preferably $R^4$ constitutes H or methyl.

Preferably $R^5$ constitutes H.

Preferably $R^5$ constitutes $C_1$-$C_6$ alkyl, $C_3$-$C_6$ cycloalkyl or $C_4$-$C_7$ lkylcycloalkyl.

Preferably $R^5$ constitutes H or methyl.

Preferably $R^8$ constitutes $CH_2OCOR^{17}$, wherein $R^{17}$ constitutes $C_1$-$C_6$ alkyl or $C_1$-$C_6$ alkenyl.

Preferably $R^9$ constitutes $C_1$-$C_6$ alkyl.

Preferably $R^{10}$ constitutes H or methyl.

Preferably $R^{11}$ constitutes H or —(C=O)—$(C_{1-4})$Alkyl.

Preferably $R^{12}$ constitutes $NR^{18}R^{19}$, wherein $R^{18}$ constitutes H or methyl and $R^{19}$ constitutes aralkyl or heteroaralkyl.

Most preferably are compounds of Formula (III),

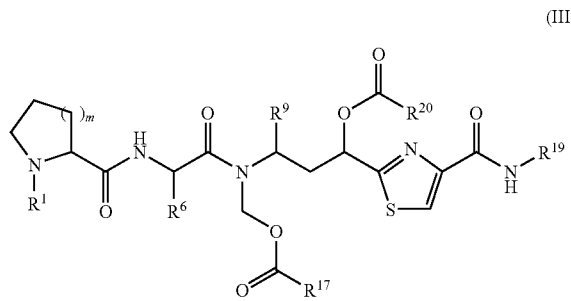

(III)

wherein $R^1$ comprise $C_1$-$C_4$ alkyl, $R^6$ comprise $C_1$-$C_6$ alkyl, $R^9$ comprise $C_1$-$C_6$ alkyl, $R^{17}$ comprise $C_1$-$C_6$ alkyl or $C_1$-$C_6$ alkenyl, $R^{19}$ comprise aralkyl or heteroaralkyl, $R^{20}$ comprise $C_1$-$C_4$ alkyl and m equals 1 or 2.

Preferentially $R^{19}$ comprise the following structure:

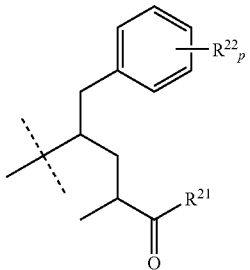

wherein $R^{21}$ comprise OH, $NH_2$, alkyloxy, alkyl amino or dialkyl amino, $R^{22}$ comprise halogen, OH, $NO_2$, $NH_1$, alkyloxy, alkyl amino or dialkyl amino and p equals 0, 1, 2 or 3.

Examples of pharmacologically acceptable salts of compounds of Formula (II) are physiologically acceptable mineral acids, e.g. hydrochloric acid, sulfuric acid, phorphoric acid or salts of organic acids, e.g. methansulfonic acid, p-toluenesulfonic acid, lactic acid, formic acid, trifluoracetic acid, citric acid, succinic acid, fumaric acid, maleic acid and salicylic acid. Compounds of Formula (II) can be solvated, especially hydrated. The hydration can occur during the synthesis process or can be a consequence of the hygroscopic nature of the originally dehydrated compound of Formula (II). Compounds of Formula (II), containing assymetric carbon atoms might exist as mixtures of diastereomers, as mixtures of enantiomers or as optically pure compounds.

The pharmaceutical composition according to the present invention is composed of at least one compound of Formula (II) and optionally carrier and/or adjuvants.

Pro drugs are also subject of the present invention and they are composed of a compound of Formula (II) and at least one pharmacologically acceptable protecting group, which is cleaved under physiological conditions, e.g. alkoxy, aralkyloxy, acyl or acyloxy, more precisely ethoxy, benzyloxy, acetyl or acetyloxy. Moreover the present invention relates to conjugates comprising at least one compound of Formula (II) and a biological macromolecule, e.g. oligo saccharide, monoclonale antibody, lectine, PSA (prostate specific antigen) or peptidic vectors and if needed as well as a suitable linker. The expression linker relates to a chemical group, which links compounds of Formula (II) with a biological macromolecule. Examples of linkers are alkyl, heteroalkyl, aryl, heteroaryl, cycloalkyl, heterocycloalkyl, aralkyl or heteroaralkyl.

The therapeutic usage of compounds of Formula (II), its pharmacologic acceptable salts and/or its solvates and hydrates, as well as the corresponding formulations and pharmacological compositions are also subject of the present invention.

The usage of the active agents for the preparation of drugs for the treatment of cancer is also subject of the present invention. Moreover the present compounds are of interest for the prevention and/or treatment of rheumatoid arthritis, inflammatory diseases, immunological diseases (e.g. type I diabetes), autoimmune diseases, other tumor diseases as well as for the surface treatment (impregnation) of plastic and metal implants, e.g. stents. In general, compounds of Formula (II) will be given as a single treatment or in combination with an arbitrary therapeutic substance according to known and accepted modes. Such therapeutically useful compositions can be administered in one of the following ways: orally, including dragees, coated tablets, pills, semi-solids, soft or hard capsules, solutions, emulsions or suspensions; parenteral, including injectable solutions; rectal as suppositories; by inhalation, including powder formulation or as a spray, transdermal or intranasal. For the production of such tablets, pills, semi solids, coated tablets, dragees and hard gelatine capsules the therapeutically used product is mixed with pharmacologically inert, anorganic or organic carriers, e.g. with lactose, sucrose, glucose, gelatine, malt, silical gel, starch, or derivatives thereof, talkum, stearinic acid or its salts, dried skim milk and the like.

For the production of soft capsules a carrier one may use for example vegetable oils, petroleum, animal or synthetic oils, wax, fat, polyols. For the production of liquid solutions and syrups one may use carriers for example water, alcohols, aqueous saline, aqueous dextrose, polyole, glycerin, vegetable oils, petroleum, animal or synthetic oils. For the production of suppositories one may use excipients as are e.g. vegetable, petroleum, animal or synthetic oils, wax, fat and polyols. For aerosol formulations one may use compressed gases suitable for this purpose, as are e.g. oxygen, nitrogen, noble gas and carbon dioxide. The pharmaceutically useful agents may also contain additives for conservation, stabilisation, e.g. UV stabilizer, emulsifier, sweetener, aromatiser, salts to change the osmotic pressure, buffers, coating additives and antioxidants.

Combinations with other therapeutic agents can include further agents, which are commonly used to treat cancer.

Compounds of Formula (IV), (V) and (VI) provided with suitable protecting groups are produced as building blocks for the of compounds of Formula (II). These can be linked via peptide coupling methods using known coupling reagents, e.g. hydroxybenzotriazole (HOBt) and diisopropylcarbodiimide (DIC) or dicyclohexylcarbodiimide (DCC).

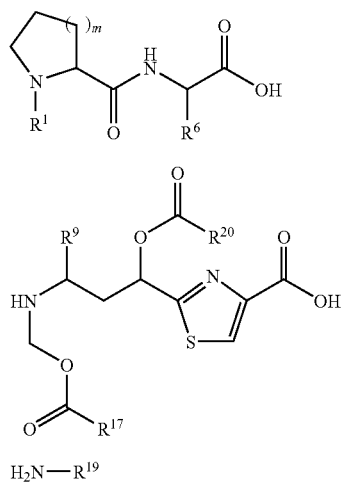

Building block (IV) can be assembled through peptide coupling of commercially available and known aminoacids.

Building block (V) can be assembled through a multicomponent reaction of starting materials of Formula (VII), (VIII) und (IX).

Herein PG is a known amino protecting group, for example tert-butyloxycarbonyl (Boc). The resulting compound can be further transformed to building block (V) using $R^{17}COOCH_2Cl$ or $H_2CO$ and $R^{17}COOH$ or $H_2CO$, TMS-Cl and $R^{17}COONa$ (I. Kornonen et al. Acta Chem. Scand. Ser. B 1982, 36(7), 467-474; R. Moriera et al. Tetrahedron Lett. 1994, 35(38), 7107-7110; R. W. A. Luke, Tetrahedron Lett. 1996, 37(2), 263-266).

Alternatively compounds of Formula (III) can be synthesized according to the following scheme:

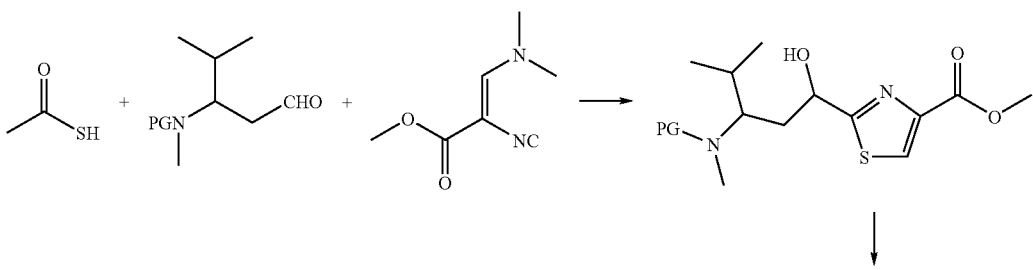

-continued
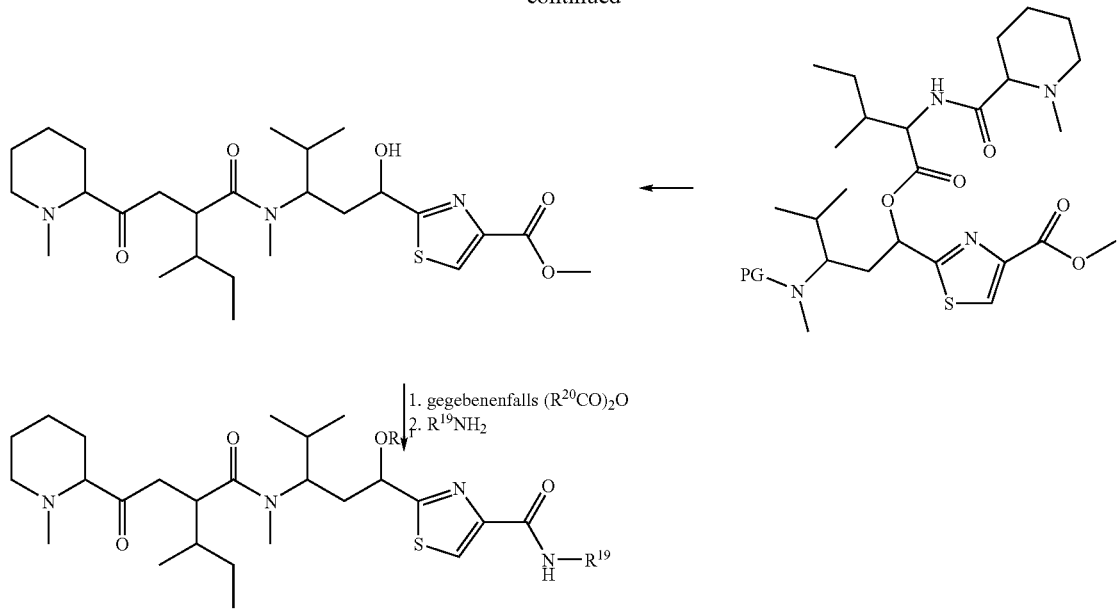
Building block (VI) of the following Formula:
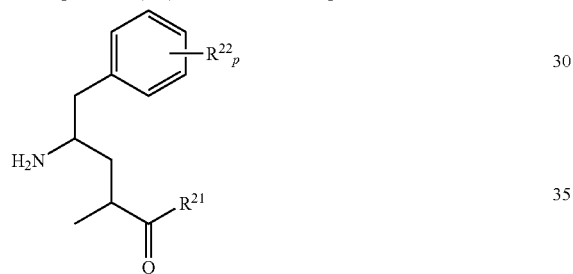
can be steteoselectively synthesized using Evens reaction.
EXAMPLES
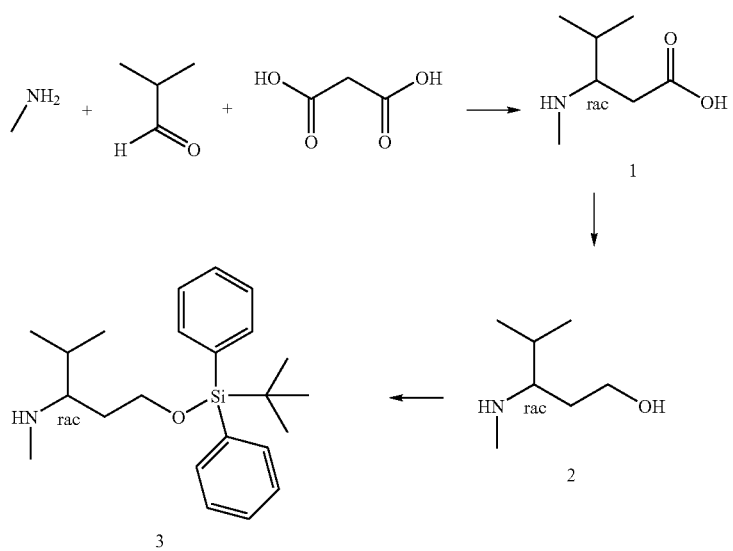

Synthesis of N-methyl-β-R,S-valine (1)

58.8 ml (0.47 mol) of a 8M methylamine solution in ethanol are slowly dropped to a solution of 33.8 g isobutyric aldehyde (0.47 mol) in 200 ml ethanol while keeping the temperature in the flask below 5° C. Then 50 ml THF are added and the mixture is refluxed for 1 h. Then 48.91 g (0.47 mol) malonic acid is added in small portions and the mixture is refluxed for 5 h. After cooling to 25° C. the precipitated is filtered off, washed with THF and dried under high vacuum. Yield: 50.34 g N-methyl-☐-R,S-valine. Mass spectroscopy: expected molecular mass 145.2; found: m/z (M+H)$^+$=146.1.

Synthese von N-Methyl-β-R,S-valinol (2)

14.5 g (0.1 mol) N-methyl-β-R,S-valine in 135 ml dry THF are added slowly to 150 ml 1M lithiumaluminium hydrid in THF (0.15 mol) while keeping the temperature in the flask below 5° C. This mixture is refluxed for 4 h. Subsequently the mixture is stirred over night. The mixture is hydrolized with 4 ml 12% KOH and 4 ml water. The precipitate is filtered off and is extracted two times with 80 ml hot THF. The filtrates are combined and the solvent is removed under vacuum. The resulting oil is distilled (bp.: 48° C./0.5 mbar). Yield: 8.28 g N-methyl-β-R,S-valinol. Mass spectroscopy: expected molecular mass 131.2; found: m/z (M+H)$^+$=132.2.

Synthesis of N-methyl-β-R,S-valinolyl-tert.-butyl-diphenyl-silylether (3)

2 g N-Methyl-β-R,S-valinole (15.24 mmol) are solubilized in 20 ml dry dichlormethan together with 465.5 mg dimethylaminopyridin (3.81 mmol) and 2.66 ml triethylamine (19.05 mmol). To this solution 4.61 ml tert.-butyldiphenylsilylchloride (18 mmol) is added and the mixture is stirred over night. 20 ml Water and 20 ml dichlormethane are added. The water phase is extracted two times with dichlormethane and the combined organic phases are dried over sodium sulfat. The sodium sulfate is filtered of and the solvent is evaporated under vacuum. The residual oil is purified using column chromatography (eluent: ethylacetat/ethanol=8:2). Yield: 3.94 g N-nethyl-β-R,S-valinolyl-tert.butyldiphenylsilylether. Mass spectroscopy: expected molecular mass 369.6; found: m/z (M+H)$^+$=370.5.

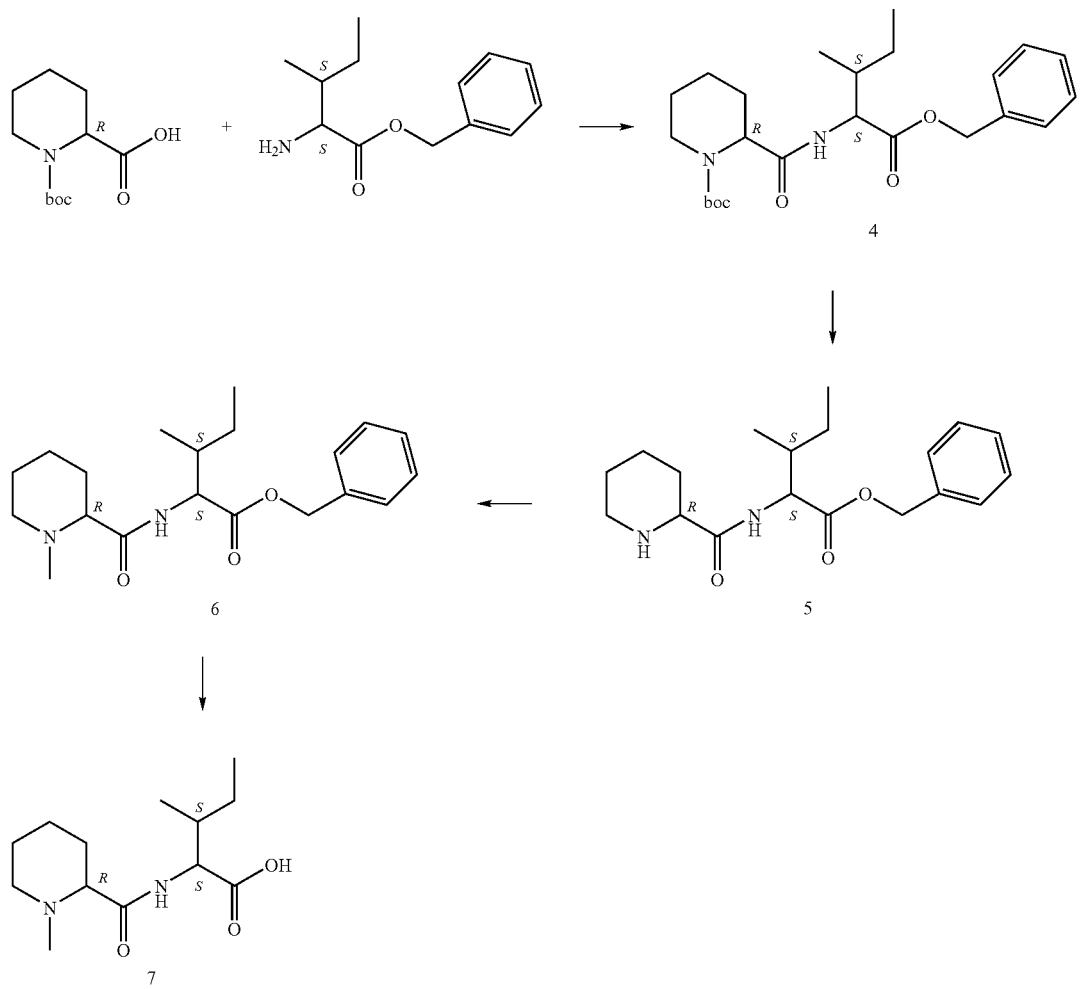

Assembly of the dipeptide (R)-N-Boc-homoPro-(S,S)-Ile-OBzl (4)

7 g 2-(1H-Benzotriazol-1-yl)-1,1,3,3-tetramethyluronium tetrafluoroborate (TBTU) (21.81 mmol) and 2.4 ml N-methylmorpholin (21.81 mmol) are added to a solution of 5 g (R)-N-Boc-homoprolin (21.81 mmol) in 40 ml dry DMF. After 10 minutes 7.21 g (S,S)-H-Ile-OBzl tosylat (18.32 mmol) and 2 ml N-methylmorpholin (18.32 mmol) are added. This mixture is stirred over night at 25° C. and then 40 ml ethylacetate are added. The organic layer is washed with saturated NaHCO₃. The aqueous layer is extracted two times with ethylacetate. The combined organic extracts are washed with saturated NaCl and dried over Na₂SO₄. The solvent is evaporated under vacuum and the pure product appears. Yield 5.54 g (R)-N-Boc-homoPro-(S,S)-Ile-OBzl. Mass spectroscopy: expected molecular mass 432.6; found: m/z (M+H)⁺=433.6

Boc-deprotection of (R)-N-Boc-homoPro-(S,S)-Ile-OBzl (5)

To a solution of (R)-N-Boc-HomoPro-(S,S)-Ile-OBzl in 60 ml dry THF is added 120 ml 4M HCl in dioxan while keeping the temperature in the flask below 5° C. After allowing the temperature to come to 20° C. the mixture is stirred for 5 h. The solvent is evaporated and can be used directly without further purification for the next step. Yield: 4.1 g (R)-H-homoPro-(S,S)-Ile-OBzl. Mass spectroscopy: expected molecular mass 332.5; found: m/z (M+H)⁺=333.6.

Reductive amination of (R)-H-homoPro-(S,S)-Ile-OBzl (6)

10 ml of a 37% formaldehyde solution (123 mmol) is added to 4.1 g (R)-homoPro-(S,S)-Ile-OBzl (12.3 mmol) in 20 ml methanol. The pH is adjusted to 5-6 with acetic acid and 1.932 g sodium cyanoborhydride (30.75 mmol) is added in portions. The mixture is stirred for 16 h at 20° C. Subsequently the reaction is acidified with conc. HCl. The solvent is evaporated under vacuum and water is added. The pH is adjusted to pH 12 with solid NaOH and the mixture is extracted three times with dichlormethan. The organic layer is dried with Na₂SO₄ and the solvent is evaporated. The resulting oil is evaporated by column chromatography (eluent: ethylacetat:n-heptan=1:1). Yield: 3.9 g (R)-N-methyl-homoPro-(S,S)-Ile-OBzl. Mass spectroscopy: expected molecular mass 346.5; found: m/z (M+H)⁺=347.4

Hydration of (R)-N-methyl-homoPro-(S,S)-Ile-OBzl (7)

To a solution of 3.9 g (R)-N-methyl-homoPro-(S,S)-Ile-OBzl (11.26 mmol) in 30 ml methanol, 1.2 g Pd (10% C) are added. The flask is first flushed with N₂ and then 10 min with H₂. Two more h the suspension is stirred under a H2-ballone; then the catalyst is filtered through celite, and washed two times with methanol. The solvent is evaporated and the residual oil is lyophylized giving a white powder. Yield: 2.7 g (R)-N-methyl-homoPro-(S,S)-Ile-OH. Mass spectroscopy: expected molecular mass 256.4; found: m/z (M+H)⁺=257.4

Coupling of (R)-N-methyl-homoPro-(S,S)-Ile-OH and N-methyl-β-R,S-valinolyl-tert.butyldiphenylsilylether (8)

To a solution of 3.522 g (R)-N-methyl-homoPro-(S,S)-Ile-OH (13.74 mmol) in 15 ml dry DMF, 2.104 g hydoxybenzotriazol (13.74 mmol) and 2.151 ml diisopropylcarbodiimide (13.74 mmol) are added. After 15 minutes stirring 4.232 g N-methyl-β-R,S-valinolyl-tert.butyldiphenylsilylether (11.45 mmol) is added and the mixture is stirred for 16 h at 20° C. The precipitated diisopropyl urea is filtered off and the solvent is evaporated under vacuum. The residue is thoroughly stirred wit dichlomethane and the residual diisopropyl urea is filtered off. The dichlormethan solution is extracted with NaHCO3 and dryed subsequently with Na2SO4. After filtering off the Na2SO4 the solvent is evaporated under

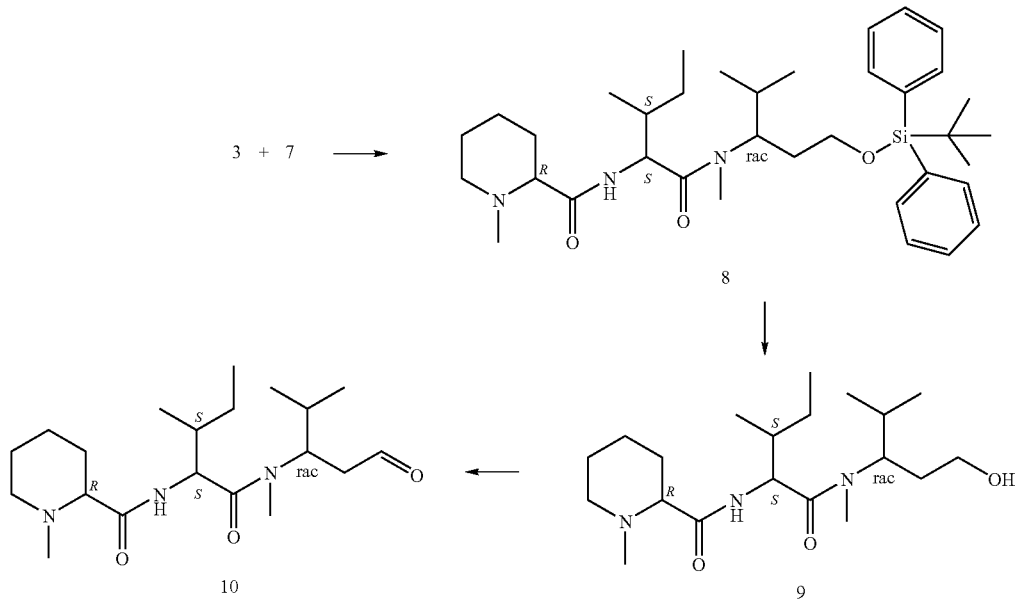

vacuum. The residue is purified with preparative HPLC. (RP-C18, eluent methanol+0.5% acetic acid/water+0.5% acetic acid). Yield: 3.91 g. Mass spectroscopy: expected molecular mass 608.0; found: m/z (M+H)$^+$=609.0.

Deprotection of the tert.butyldiphenylsilyl Protecting Group of (8) (9)

3.91 g Of compound 8 (6.43 mmol) are solubilized in 30 ml dry tetrahydrofuran and 2.223 ml tetrabutylammoniumfluorid (1M in THF) (7.72 mmol) are added dropwise and the resulting mixture is stirred for 2 h at 20° C. Then 8 ml of water is added and the tetrahydrofuran is evaporated under vacuum. The solution is neutralized and extracted five times with ethylacetat. The combined organic phases are extracted two times with saturated NaCl and dried over Na$_2$SO$_4$. The Na$_2$SO$_4$ is filtered off and the solvent is evaporated. The resulting product is pure enough for further transformations. Mass spectroscopy: expected molecular mass 369.6; found: m/z (M+H)$^+$=370.5.

Swern-Oxidation of (9) (10)

A solution of 0.665 ml oxalylchloride (7.75 mmol) in 25 ml dry dichlormethan in a 250 ml flask is cooled to −70° C. under a N$_2$ atmosphere. Slowly 1.188 ml dimethylsulfoxide (16.73 mmol) in 5 ml dry dichlormethane is added in a way that the inner temperature is kept below −60° C. and the resulting mixture is stirred for 30 minutes at −70° C. Then a solution (6 ml) of (9) (6.43 mmol) in dichlormethane is added in a way that the inner temperature is kept below −60° C. After stirring for further 30 minutes 4.459 ml triethylamin (32.17 mmol) are added at −70° C. Once the flask reached 20° C., 15 ml water are added and further 10 minutes are stirred. The aqueous phase is extracted two times with dichlormethan. The combined orgaic phases are dryed over Na$_2$SO$_4$, the Na$_2$SO$_4$ is filtered off and the solvent is evaporated. The resulting product is pure enough to be used in the next step. Mass spectroscopy: expected molecular mass 367.6; found: m/z (M+H)$^+$=368.5.

Thiazolsynthesis (11)

0.695 ml Methylamin solution (33% in ethanol) (7.72 mmol) are added to (10) in 20 ml dry methanol and stirred for 1 h at 20° C. 991.3 mg 3-Dimethylamino-2-isocyano-acrylacidmethylester (6.43 mmol) and 0.457 ml thioacetic acid (6.43 mmol) are added and stirred for 16 h at 20° C. The solvent is evaporate under vacuum and the residue is purified by preparative HPLC (reversed phase-C18-phase, eluent methanol+0.5% acetic acid/water+0.5% acetic acid). Yield: 1.294 g. Mass spectroscopy: expected molecular mass 565.8; found: m/z (M+H)$^+$=566.7

11 →

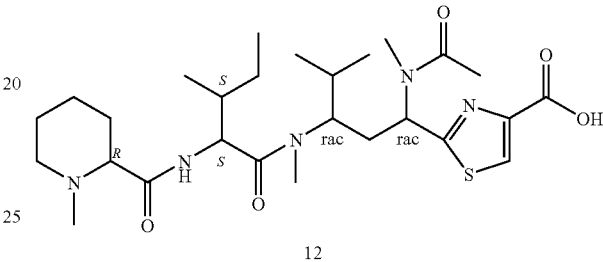

12

Saponification (11) (12)

To a solution of 1.294 g (11) (2.29 mmol) in 20 ml THF 220 mg LiOH (9.16 mmol) in 20 ml water rare added and stirred for 16 h at 20° C. This mixture is neutralized with 2N HCl. The solvent is evaporated under reduced pressure and the residue is purified with preparative HPLC (reversed phase-C18-phase, eluent methanol+0.5% acetic acid/water+0.5% acetic acid). Yield: 1.14 g. Mass spectroscopy: expected molecular mass 551.8; found: m/z (M+H)$^+$=552.7

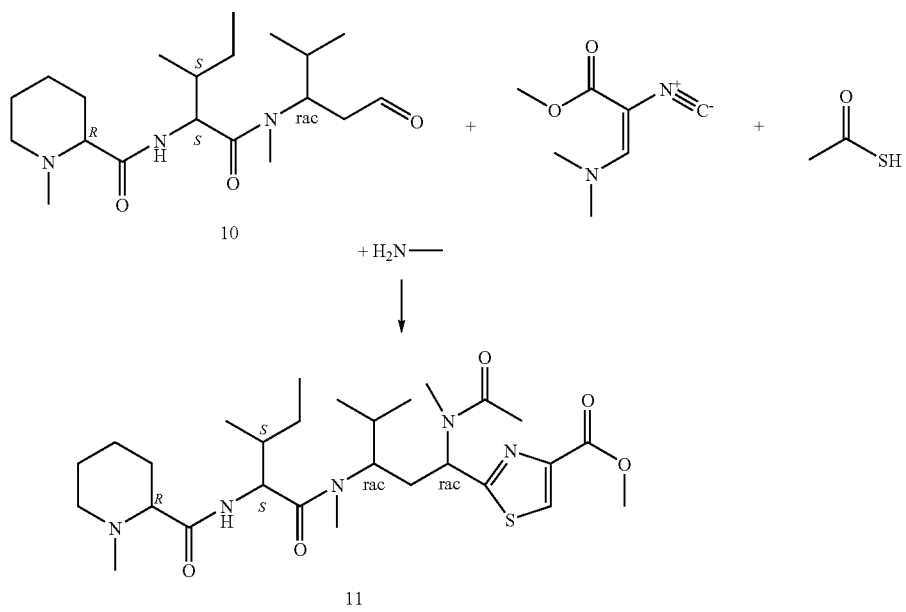

12 →

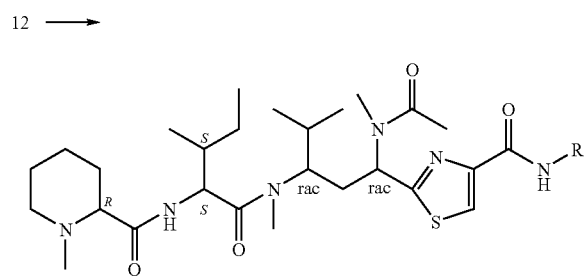

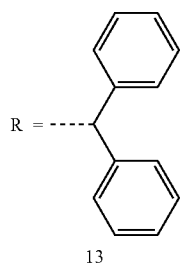
13

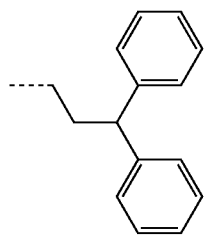
14

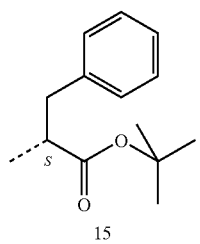
15

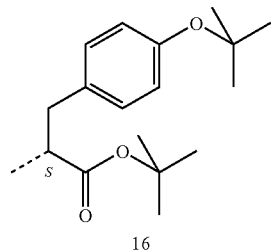
16

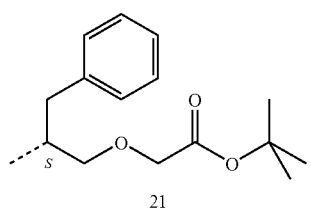
21

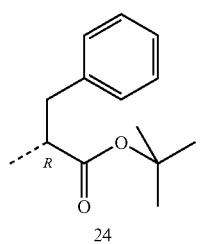
24

13, 14,
15, 16,
21, 23, 24 →

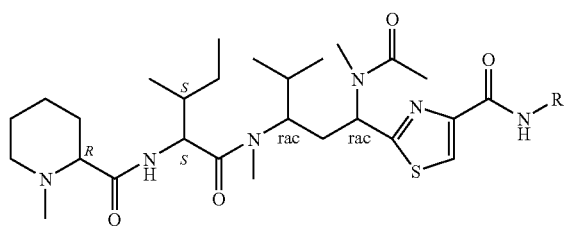

-continued

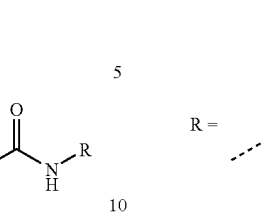

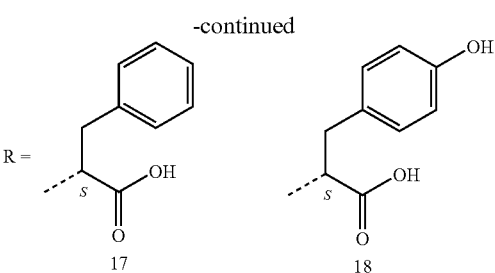

17    18

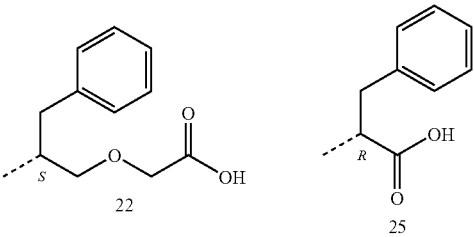

22    25

Coupling of (12) and □-aminodiphenylmethane (13)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 0.062 ml α-aminodiphenylmethan (0.36 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 717.0; found: m/z (M+H)$^+$=718.1

Coupling of (12) and 3,3-diphenylpropylamine (14)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 76 mg 3,3-diphenylpropylamin (0.36 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 745.0; found: m/z (M+H)$^+$=746.1.

Coupling of (12) and S-phenylalanine tert.butylester (15)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 24.3 mg S-phenylalanine tert.butylester (0.11 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 755.0; found: m/z (M+H)$^+$=756.2.

Coupling of (12) and S-tyrosin-O-tert.-butylether-tert.-butylester (16)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 32.3 mg S-tyrosin-O-tert.-butylether-tert.-butylester (0.11 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 827.1; found: m/z (M+H)$^+$=828.0.

Deprotection of (15) (17)

To a solution of 26 mg (15) (0.034 mmol) 2 ml dry dichlormethan 2 ml trifluoracetic acid are added. The mixture is stirred for 1 h and the solvent is evaporated under the addition of n-heptan. The product is pure. Yield: 20 mg. Mass spectroscopy: expected molecular mass 698.9; found: m/z (M+H)$^+$=699.5.

Deprotection of (16) (17)

To a solution of 26 mg (16) (0.034 mmol) 2 ml dry dichlormethan 2 ml trifluor acetic acid are added. The mixture is stirred for 1 h and the solvent is evaporated under the addition of n-heptan. The product is pure. Yield: 18 mg. Mass spectroscopy: expected molecular mass 714.9; found: m/z (M+H)$^+$=715.5.

Coupling of benzyloxycarbonyl-S-phenylalaninol and bromo aceticacid-tert.-butyl-ester (19)

To a solution of 1.141 g benzyloxycarbonyl-S-phenylalaninol (4 mmol) in 20 ml dry THF 160 mg sodiumhydrid dispersion (60% in mineral oel) are added. After end of H$_2$ evolution 1.182 ml bromo acetic acid tert.-butylester (8 mmol) are added and the mixture is stirred for 48 h at 20° C. The solvent is evaporated under reduced pressure and the product is purified with preparative HPLC (reversed phase-C18-phase, eluent methanol+0.5% acetic acid/water+0.5% acetci acid). Yield: 805 mg. Mass spectroscopy: expected molecular mass 399.5; found: m/z (M+H)$^+$=400.3

Cbz-deprotection of (19) (20)

To a solution of 805 mg (19) (2.02 mmol) in 15 ml methanol, 800 mg Pd (10% C) are added. The flask is first flushed with N$_2$ and then stirred 16 h under H2 atmosphere (2 H2 ballons). The catalyst is filtered through celite and washed several times with methanol. The solvent is evaporated. Yield: 482 mg. Mass spectroscopy: expected molecular mass 265.4; found: m/z (M+H)$^+$=266.3.

Coupling of (12) and (20) (21)

To a solution of 49.5 mg (12) (0.09 mmol) in 3 ml dry DMF 16.8 mg hydroxybenzotriazol hydrate (0.11 mmol) and 0.014 ml diisopropylcarbodiimid (0.11 mmol) are added. After stirring for 15 minutes at 20° C. 29.2 mg (20) (0.11 mmol) are added. After stirring over night at 20° C. the solution is filtered and the residue is purified by HPLC (reversed phase-C18-phase, eluent methanol+0.5% acetic acid/water+0.5% acetic acid). Yield: 22 mg. Mass spectroscopy: expected molecular mass 799.1; found: m/z (M+H)$^+$=800.2.

Deprotection of (21) (22)

To a solution of 22 mg (21) (0.028 mmol) in 2 ml dry dichlormethan 2 ml trifluoracetic acid are added. This mixture is stirred for 1 h at 20° C. and the solvent is evaporated upon addition of n-heptan. The product is pure. Yield: 16 mg. Mass spectroscopy: expected molecular mass 757.0; found: m/z (M+H)$^+$=758.2.

Coupling of (12) and methylamin (23)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 0.22 ml methylamin solution (2M in THF) (0.44 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 564.8; found: m/z (M+H)$^+$=565.7.

Coupling of (12) and R-Phenylalanintert.butylester (24)

To a solution of 49.5 mg (12) (0.09 mmol) in 3 ml dry DMF 18.6 mg 6-chlorhydroxybenzotriazole (0.11 mmol) and 0.014 ml diisopropylcarbodiimide (0.11 mmol) are added. This mixture is stirred for 15 minutes at 20° C. and 24.3 mg R-phenylalanine tert.butylester (0.11 mmol) are added. This mixture is stirred over night at 20° C., then the solution is filtered and the solvent is evaporated under vacuum. The residue is purified by perperative HPLC (reversed phase-C18-phase, eluent methanol+0.5% acetic acid/water+0.5% acetic acid). Yield: 35 mg. Mass spectroscopy: expected molecular mass 755.0; found: m/z (M+H)$^+$=756.2.

Deprotection of (24) (25)

To a solution of 23 mg (24) (0.03 mmol) in 2 ml dry dichlormethan 2 ml trifluoracetic acid are added. The mixture is stirred for 1 h and the solvent is evaporated under the addition of n-heptan. The product is pure. Yield: 18 mg. Mass spectroscopy: expected molecular mass 698.9; found: m/z (M+H)$^+$=699.5.

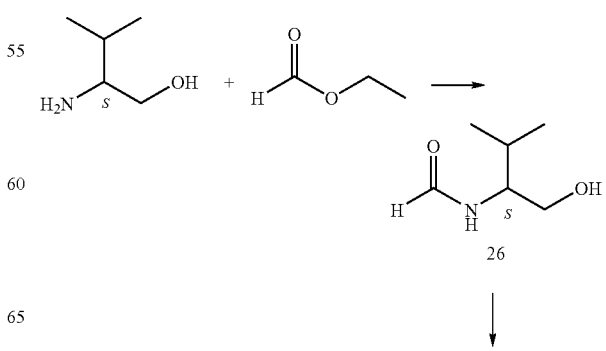

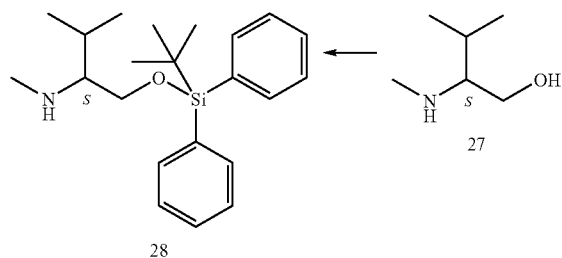

Synthesis of N-formyl-S-valinol (26)

10 g S-Valinol (97 mmol) are dissolved in 50 ml ethylformiat and refluxed for 1 h. The solvent is evaporated and the residue is distilled under vacuum (bp.: 153° C./0.5 mbar). Yield: 8.4 g. Mass spectroscopy: expected molecular mass 131.2; found: m/z $(M+H)^+=132.3$

Synthesis of N-methyl-S-valinol (27)

To a solution of 5.7 g lithiumaluminiumhydrid (150 mmol) in 200 ml dry THF, 8.4 g N-formyl-S-valinol (64 mmol) dissolved in 40 ml dry THF are added slowly and stirred for 16 h at 20° C. In several portions 30 g sodium sulfat decahydrat and 18 ml water are added and furthermore stirred for 3 h at 20° C. The solids are filtered off and the solvent is evaporated under vacuum. The residual material is purified by destillation (bp.: 93° C./54 mbar). Yield: 3.7 g. Mass spectroscopy: expected molecular mass 1.17.2 found: m/z $(M+H)^+=118.1$.

Synthesis of N-methyl-S-valinolyl-tert.butyldiphenylether (28)

To a solution of 1.64 g N-methyl-S-valinol (14 mmol) in 10 ml dry dichlormethane 427 mg dimethylaminopyridine (3.5 mmol) and 2.44 ml triethylamin (17.5 mmol) are added. Then 4.3 ml tert.butyldiphenylsilyl chloride are added and 16 h stirred at 20° C. Then 10 ml water and THF are added and the phases are separated. The aqueous phase id extracted two times with dichlormethane. The combined organic phases are dried over $Na_2SO_4$, subsequently the solvent is evaporated. The residue is purified by column chromatography (eluent: ethylacetat/ethanol=8:2). Yield: 3.16 g. Mass spectroscopy: expected molecular mass 355.6 found: m/z $(M+H)^+=366.6$

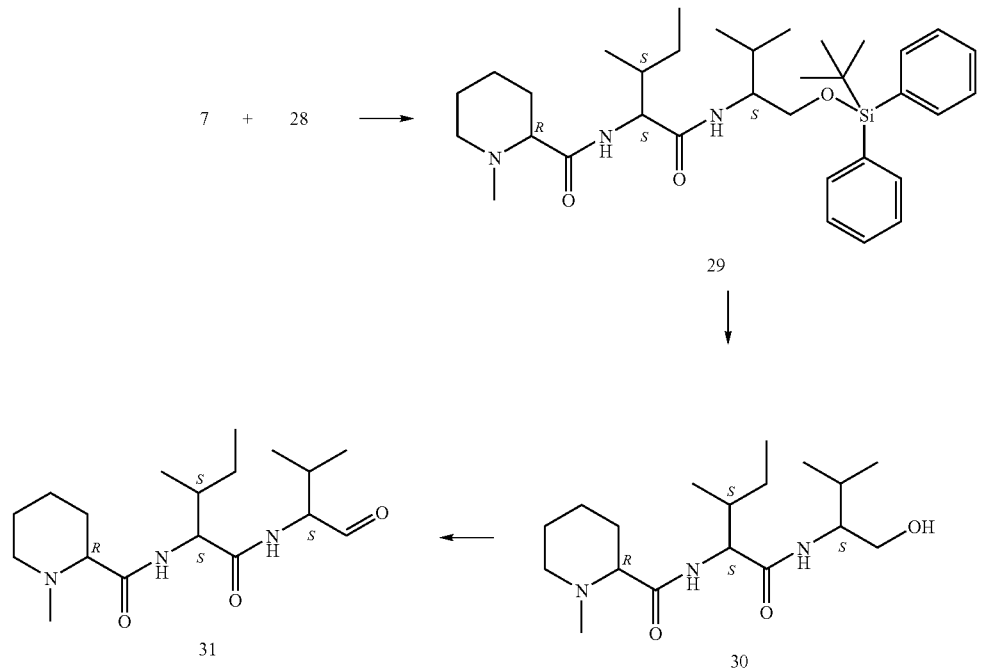

Coupling of (R)-N-methyl-homoPro-(S,S)-Ile-OH and N-methyl-S-valinolyl-tert.butyldiphenylsilylether (29)

To a solution of 1.54 g (R)-N-methyl-homoPro-(S,S)-Ile-OH (6 mmol) in 10 ml dry DMF, 1.02 g 6-chlorohydroxybenzotriazol (6 mmol) and 0.939 ml diisopropylcarbodiimid (6 mmol) are added. The mixture is stirred for 15 minutes and 2.56 g N-ethyl-S-valinolyl-tert.butyldiphenylether (7.2 mmol) are added and stirred for 16 h at 20° C. Then the solvent is evaporated under vacuum and the residue is purified by preparative HPLC (reversed phase-C18-phase, eluent methanol+0.5% acetic acid/water+0.5% acetic acid). Yield: 1.06 g. Mass spectroscopy: expected molecular mass 593.9 found: m/z (M+H)$^+$=594.8.

Cleavage of the tert.-butyldiphenylsilyl protecting group of (29) (30)

To a solution of 1.06 g (29) (1.79 mmol) in 10 ml dry THF a solution of 2.15 ml tetrabutylammoniumfluorid (1M Lösung in THF) (2.15 mmol) is added. The mixture is stirred for 16 h at 20° C. and then hydrolysed upon addition of 3 ml water. The organic solvent is evaporated and the aqueous phase is extracted five times with ethylacetat. The combined organic phases are washed with saturated NaIl and dried over Na$_2$SO$_4$. After filtration of Na$_2$SO$_4$ the solvent is evaporated. Yield: 1.05 g (some residual silyl is remaining). Mass spectroscopy: expected molecular mass 355.5 found: m/z (M+H)$^+$=356.5.

Swern-Oxidation of (30) (31)

0.316 ml Oxalylchlorid (1.98 mmol,) are solubilized in 3 ml dry dichlormethan in a 100 ml flask under N$_2$ atmosphere and cooled to −70° C. To this solution 0.305 ml dimethylsulfoxid (4.29 mmol) in 0.6 ml dichlormethan are added slowly (evolution of gas, keep the temperature below −60° C.) and stirring continues for 30 minutes. A solution of 587 mg (30) (1.65 mmol) in 2 ml dichlormethan is added while keeping the temperature below −60° C. and stirring for 30 minutes. Then 1.146 ml triethylamin (8.25 mmol) is added. The mixture is allowed to come to 20° C. and then 10 ml water are added and the mixture is stirred for another 10 minutes. The aqueous phase is extracted two times with dichlormethan. The combined organic layers are dried with Na$_2$SO$_4$. After filtering off the Na$_2$SO$_4$ the solvent is evaporated. Yield: 636 mg. Mass spectroscopy: expected molecular mass 353.5 found: m/z (M+H)$^+$=354.5.

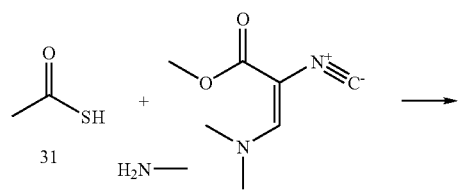

31

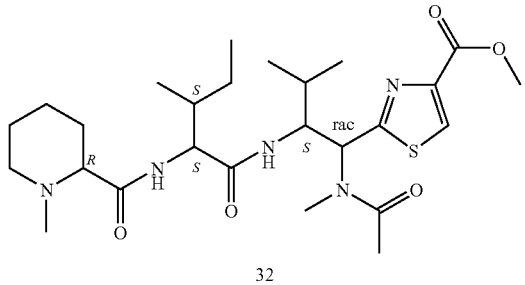

32

Thiazolsynthesis (32)

636 Mg (31) (1.15 mmol) and 0.173 ml methylamin (33% in ethanol) (1.38 mmol) in 3 ml dry methanol are stirred for 1 h at 20° C. 185 mg 3-Dimethylamino-2-isocyano-acrylciacidmethylester (1.2 mmol) and 0.086 ml thioacetic acid (1.2 mmol) are added and stirred for 16 h at 20° C. The solvent is evaporated and the residue is purified with preparative HPLC (reversed phase-C18-phase, eluent methanol+0.5% acetic acid/water+0.5% acetic acid). Yield: 150 mg. Mass spectroscopy: expected molecular mass 551.8; found: m/z (M+H)$^+$=552.7.

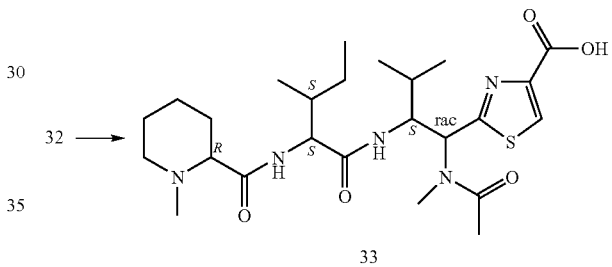

33

Saponification of (32) (33)

To a solution of 61 g (32) (0.11 mmol) in 2 ml THF, 10.6 mg LiOH (0.44 mmol) in 2 ml water is added and stirred for 16 h at 20° C. The mixture is neutralized with 2N HCl. The solvent is evaporated and the residue is purified with preparative HPLC (reversed phase-C18-phase, eluent methanol+0.5% acetic acid/water+0.5% acetic acid). Yield: 50 mg. Mass spectroscopy: expected molecular mass 537.7; found: m/z (M+H)$^+$=538.7.

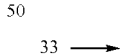

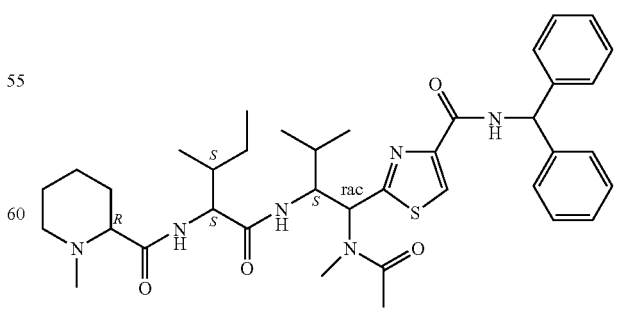

34

Coupling of (33) and α-aminodiphenylmethane (34)

To a solution of 49.5 mg (33) (0.093 mmol) in 3 ml dry DMF, 14.2 mg hydroxybenzotriazol (0.093 mmol) and 0.012 ml diisopropylcarbodiimid (0.093 mmol) are added and stirred for 15 minutes at 20° C. 0.064 ml α-aminodiphenyl-methan (0.372 mmol) is added and is stirred over night. The mixture is filtered and evaporated and the residue is purified by preparative HPLC (reversed phase-C18-phase, eluent methanol+0.5% acetic acid/water+0.5% acetic acid). Yield: 30 mg. Mass spectroscopy: expected molecular mass 703.0; found: m/z (M+H)$^+$=704.1.

General Procedure for the Synthesis of Thiazoles

1 Mmol of the carbonyl compound (IX) is solubilized in 3 ml dry THF gelost under $N_2$ atmosphere and 1 mmol borontrifluorid etherat are added. After 10 min 1 mmol of isocyanide (VIII) and 1 mmol of thioacarboxylic acid (VII) are added and stirred for 72 h. Water is added and optinally filtered through celite. The solvent is evaporated under vacuum. The residue is solubilized in ethylacetate. The organic phase is washed two times with water. After drying the organic phase over $Na_2SO_4$ the solvent is evaporated. The residue is purified by preparative HPLC (reversed phase-C18-phase, eluent methanol+0.5% acetic acid/water+0.5% acetic acid).

Compounds of Formula (IX) can be synthesized for example by a α-aminoalkylation of isobutyric aldehyd, ammoniumacetat or a primary amine or amine hydrochlorid and malonic acid:

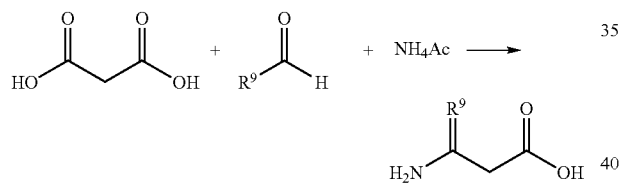

The resulting β-amino acid can be subsequently N-alky-lated (e.g. by reductive amination) and protected (e.g. t-butyloxycarbonyl, Boc). Then the carboxylic acid group is transformed to the aldehyde (e.g. by reduction to the alcohol by LiAlH$_4$ and subsequent Swern oxidation to the aldehyde; see for example R. C. Larock, Comprehensive Organic Transformations, VCH Publishers, New York, 1989). Alternatively the β-aminoacid can be synthesized by a Arndt-Eistert procedure starting from valine.

Example 35

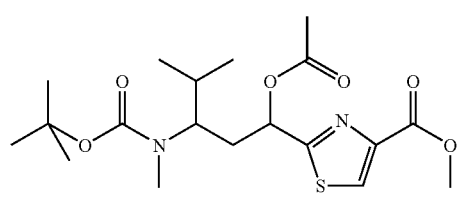

$C_{19}H_{30}N_2O_6S$ (414.5248)
MS (ESI): 415 [M+H]

Example 36

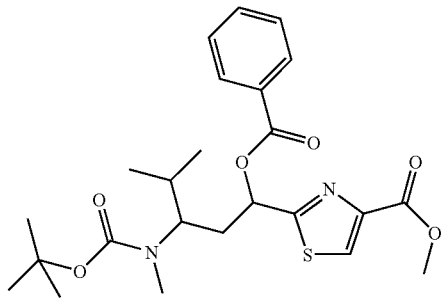

$C_{24}H_{32}N_2O_6S$ (476.5964)
MS (ESI): 477 [M+H]

Example 37

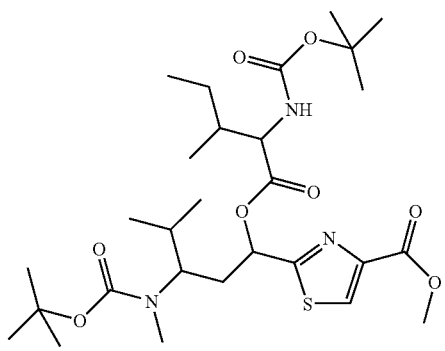

$C_{28}H_{47}N_3O_8S$ (585.7661)
MS (ESI): 586 [M+H]

Example 38

A compound from example 35 (0.1 mmol) is stirred in 2 ml dichlormethan (DCM) and 0.1 ml trifluoracetic acid (TFA) for 1 h at 20° C. The liquides DCM/TFA are evaporated and the residue is purified by HPLC.

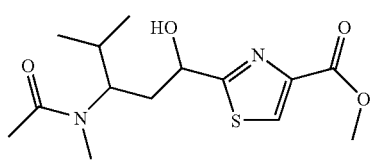

$C_{14}H_{22}N_2O_4S$ (314.4064)
MS (ESI): 315 [M+H]

Example 39

The compound from example 37 (0.1 mmol) is dissolved in 2 ml Dichloromethan (DCM) and 0.1 ml trifluoracetic acid (TFA) is added and stirred for 1 h at 20° C. The liquides DCM/TFA are evaporated and the residue is purified by HPLC.

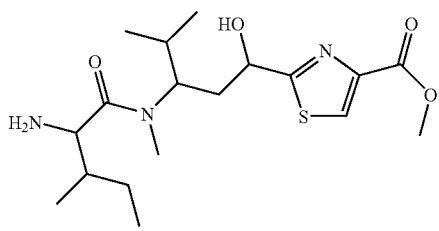

C$_{18}$H$_{31}$N$_3$O$_4$S (385.5295)
MS (ESI): 386 [M+H]
Bispiel 40:

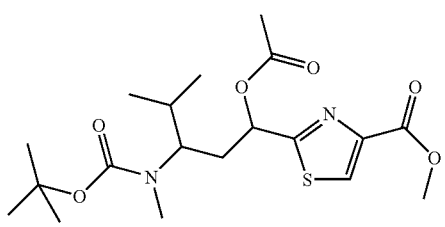

C$_{18}$H$_{28}$N$_2$O$_6$S (400.4977)
MS (ESI): 401 [M+H]

Example 41

1 mmol of the compound from example 40 in 1 ml methanol is stirred with 1 ml 4 M ammonia solution in methanol for 2 h at 20° C. Tsolvent is evaporated under vacuum.

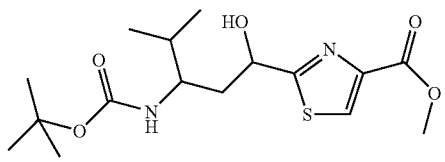

C$_{16}$H$_{26}$N$_2$O$_5$S (358.4600) MS (ESI): 381 [M+Na]

Examples 42 and 43

Ester Coupling of Hydroxythiazols (Example 41) and Dipeptide (7) and Subsequent Transacylation To 2 Mmol (512 mg) 3-methyl-2-[(1-methyl-piperidin-2-carbonyl)-amino]-pentanoic acid (7) in 5 ml dry dichlormethan is added 2 mmol (252 mg) N,N'-diisopropylcarbodiimide (DIC) in 2.5 ml DCM and 0,2 mmol (24 mg) DMAP in 2.5 ml DCM under N$_2$ atmosphere at 0° C. The mixture is stirred 5 minutes at 0° C. 1 mmol (372 mg) 2-[3-(tert.-butoxycarbonyl-methylamino)-1-hydroxy-4-methyl-pentyl]-thiazole-4-carboxylic acid methylester (example 41) is dissolved in 5 ml DCM and slowly added via syringe. The mixture is stirred 4 h at 20° C. The mixture concentrated in vacuum and the precipitated urea is filtered off. To the filtrate is added 1 ml of trifluoracetic acid and 1 h stirred at 20° C. and the solvents are evaporated under vacuum. The residue is dissolved in 1 ml dry dichlormethan and 1 ml triethylamin is added and 1 h stirred at 20° C. The solvent is evaporated under vacuum. The rearranged coupling product is purified by HPLC.

2-(3-(tert.-butoxycarbonyl-methyl-amino)-4-methyl-1-{3-methyl-2-[(1-methyl-piperidin-2-carbonyl)-amino]-pentanoyloxy}-pentyl)-thiazol-4-carboxylic acid methylester (42)

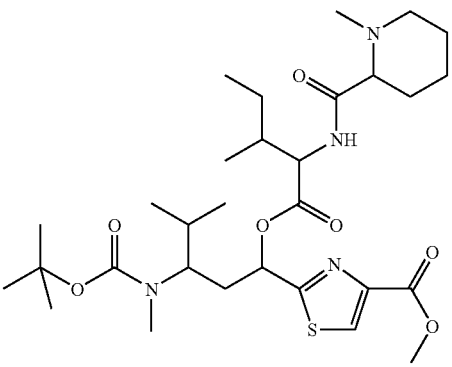

C$_{30}$H$_{50}$N$_4$O$_7$S (610,82)
MS (ESI): 611 [M+H]; 633 [M+Na]

2-[1-Hydroxy-4-methyl-3-(methyl-{3-methyl-2-[(1-methyl-piperidin-2-carbonyl)-amino]-pentanoyl}-amino)-pentyl]-thiazol-4-carboxylic acid methylester (43)

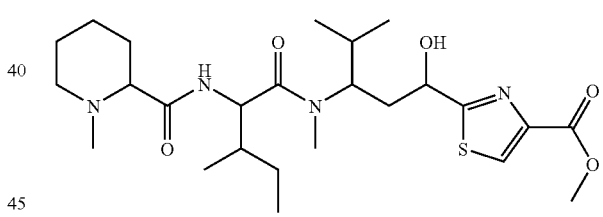

C$_{25}$H$_{42}$N$_4$O$_5$S (510,70)
MS (ESI): 511 [M+H]; 533 [M+Na]

Examples 44 and 45

Reaction of (43) and Phenylethylamine and Subsequent Acetylation 0.14 Mmol (72 mg) 2-[1-hydroxy-4-methyl-3-(methyl-{3-methyl-2-[(1-methylpiperidine-2-carbonyl)-amino]-pentanoyl}-amino)-pentyl]-thiazol-4-carboxylic acid methylester (43) are stirred with 100 μl phenylethylamine for 12 h at 20° C. The reaction mixture is filtered through a plug of silica gel and washed with ethylacetate. The mixture is evaporated to dryness and 40 μl acetic acid anhydride and 10 μl pyridine are added. The mixture is stirred for 2 h at 20° C. A third of the reaction mixture is purified with a analytical HPLC.

1-methyl-piperidin-2-carbonsäure-[1-({1-[2-hydroxy-2-(4-phenethylcarbamoyl-thiazol-2-yl)-ethyl]-2-methyl-propyl}-methylcarbamoyl)-2-methyl-butyl]-amide (44)

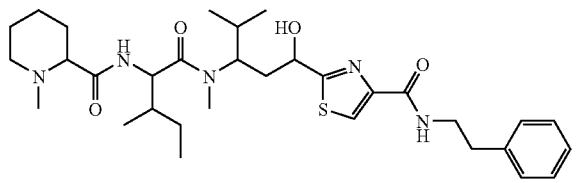

$C_{32}H_{549}N_5O_4S$ (599,84)
MS (ESI): 600 [M+H]; 622 [M+Na]

Acetic acid 4-methyl-3-(methyl-{3-methyl-2-[(1-methyl-piperidine-2-carbonyl)-amino]-pentanoyl}-amino)-1- (4-phenethylcarbamoyl-thiazol-2-yl)-pentylester (45)

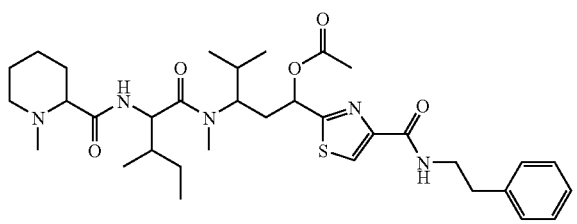

$C_{34}H_{51}N_5O_5S$ (641,88)
MS (ESI): 642 [M+H]; 664 [M+Na]

Synthesis of Building Block (VI) According to Evans-Procedure

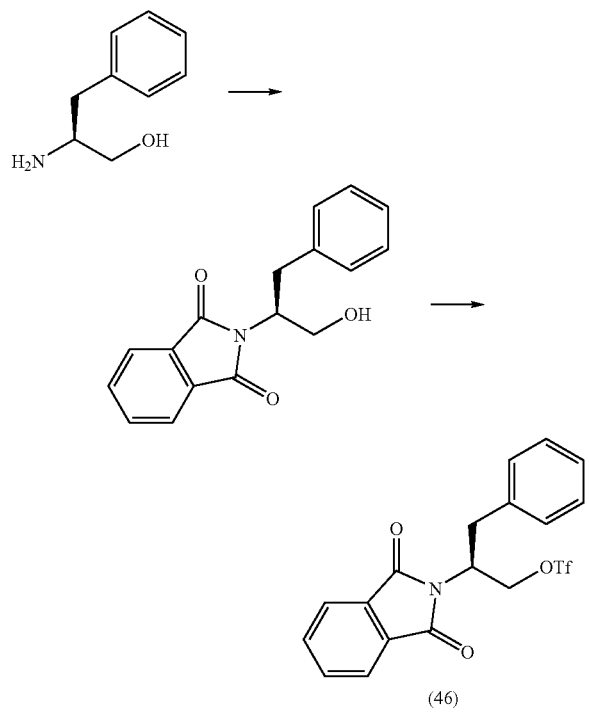

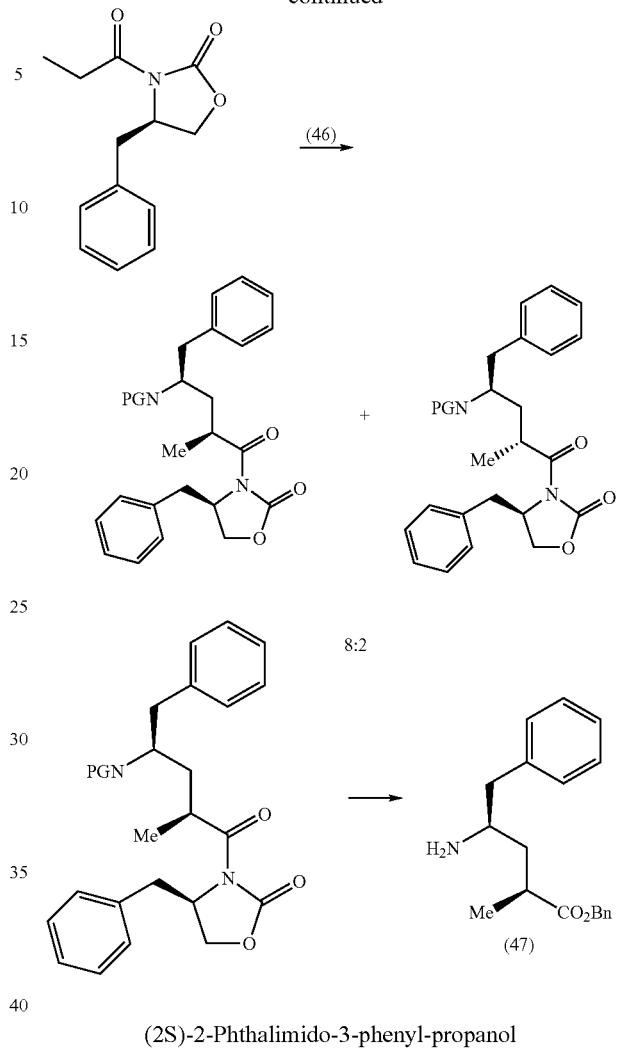

(2S)-2-Phthalimido-3-phenyl-propanol

To L-phenylalaninol (1.0 g, 6.61 mmol) and $Na_2CO_3$ (1.05 g, 9.92 mmol) in a 1:1 mixture of THF (10 mL) and $H_2O$ (10 mL) N-carbethoxyphthalimide (1.74 g, 7.94 mmol) is added and stirred 4 h at 20° C. To this reaction mixture ethylacetate (20 mL) is added. The aqueous phase is extracted two times with 15 mL ethylacetate and the combined organic phases are washed with saturated NaCl, dried with $Na_2SO_4$ and the solvent is evaporated under vacuum. The product is purified with column chromatography using 2% MeOH in $CH_2Cl_2$. Yield: 1.41 g (76%); MS (ESI) 282 [M+H]; $^1$H NMR (300 MHz, $CDCl_3$): δ 7.82-7.76 (m, 2H), 7.73-7.66 (m, 2H), 7.24-7.12 (m, 5H), 4.70-4.58 (m, 1H), 4.12-4.02 (m, 1H), 3.98-3.88 (m, 1H), 3.20 (d, J=12.5 Hz, 2H), 2.80-2.72 (m, 1H).

(2S)-1-Trifluoromethanesulfonyl-2-phthalimido-3-phenyl propanoat

To a solution of (2S)-2-phthalimido-3-phenylpropanole (0.42 g, 1.49 mmol) in dry $CH_2Cl_2$ (5 mL), pyridin (146 µL, 1.79 mmol) is added at −78° C. and stirred for 20 minutes. To this mixture 3 min trifluoromethansulfonic acid anhydride (264 µL, 1.57 mmol) is added in between 3 minutes and stirred for 1 h at −78° C. The reaction mixture is quenched with 3 ml saturated NaCl. The aqueous phase is extracted with 5 mL of $CH_2Cl_2$, the combined organic phases are washed with 5 ml saturated NaCl gewaschen, dried with $Na_2SO_4$ and the solvent is evaporated. The product is purified with column chromatography using 20% ethylacetat in hexen. Yield: 0.41 g (66%). MS (ESI) 414 [M+H]; $^1$H NMR (300 MHz, CDCl$_3$): δ 7.84-7.77 (m, 2H), 7.75-7.68 (m, 2H), 7.28-7.14 (m, 5H), 5.18 (t, J=13.0 Hz, 1H), 5.00-4.85 (m, 1H), 4.55-4.30 (m, 1H), 3.40-3.25 (m, 2H).

Evans Alkylation (4R)-3-propanoyl-4-benzyl-2-oxazolidinone (0.100 g, 0.43 mmol) is dissolved in 2 ml dry THF in an argon atmosphere and subsequently cooled to −40° C. LiHMDS (1M/THF) (0.47 mL, 0.47 mmol) is added and stirred for 45 minutes. (2S)-1-Trifluoromethansulfonyl-2-phthalimido-3-phenylpropanoate (0.266 g, 0.64 mmol) in dry THF (2 mL) is added. The mixture is stirred for 4 h at −40° C. and subsequently quenched with 3 ml saturated NaCl. The aqueous phase is extracted 2 times with 5 ml ethylacetate. The combined organic phases are washed with 3 ml saturated NaCl, dried with Na$_2$SO$_4$ and the solvent is evaporated under vacuum. The product is purified with column chromatography using 25% ethylacetate in hexen. Yield: 0.149 g (70%). The diastereomers can be separated using preparative TLC. The wanted diastereomer is formed in excess: 8:2.

(2'S,4'R,4R,)-3-(2'Methyl-4'phthalimido-5'phenyl pentanoyl)-4-benzyl-1,3-oxazolidin-2-one (Major Product)

MS (ESI): 497 [M+H]; $^1$H NMR (300 MHz, CDCl$_3$): δ 7.77 (t, J=8.5 Hz, 2H), 7.63 (t, J=8.4 Hz, 1H), 7.55 (t, J=8.4 Hz, 1H), 7.42 (d, J=8.5 Hz, 2H), 7.37-7.22 (m, 6H), 7.10 (d, J=8.6 Hz, 2H), 5.08 (q, J=9.6 and 16.1 Hz, 1H), 4.56-4.42 (m, 2H), 4.20-4.00 (m, 4H), 3.45 (dd, J=10.7 and 16.1 Hz, 1H), 3.12-2.98 (m, 2H), 2.34 (dd, J=12.8 and 13.9 Hz, 1H), 1.62 (d, J=8.6 Hz, 3H).

(2'R,4'R,4R,)-3-(2'Methyl-4'phthalimido-5'phenyl pentanoyl)-4-benzyl-1,3-oxazolidin-2-one (Minor Product)

MS (ESI): 497 [M+H]; $^1$H NMR (300 MHz, CDCl$_3$): δ 8.12 (d, J=8.6 Hz, 1H), 7.76 (d, J=8.5 Hz, 1H), 7.63 (t, J=8.6 Hz, 1H), 7.53 (t, J=8.5 Hz, 1H), 7.40-7.20 (m, 10H), 5.10 (q, J=7.5 and 15.0 Hz, 1H), 4.94-4.84 (m, 1H), 4.54-4.42 (m, 1H), 4.36-4.08 (m, 4H), 3.46-3.30 (m, 2H), 3.12 (dd, J=9.6 and 11.8 Hz, 1H), 2.88 (dd, J=9.5 and 12.8 Hz, 1H), 1.00 (d, J=9.6 Hz, 3H).

Cleavage of the oxazolidinons: Evans et. al., J. Am. Chem. Soc. 1982, 104, 1737-1739.

Deprotection of the phthalimids: using hydrazine/EtOH at 20° C.: Sasaki, T. et. al., J. Org. Chem. 1978, 43, 2320; Khan, M. N. et. al., J. Org. Chem. 1995, 60, 4536.

According to the herein disclosed synthetic procedures also the following tubulysin derivatives where synthesized:

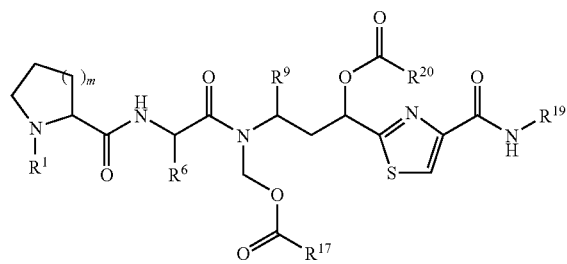

The following residues where used:

m=0, 1, 2, 3;

$R^1$=methyl, ethyl;

$R^6$=isopropyl, isobutyl, ethyl, cyclopropyl, CH$_2$-cyclopropyl, CH(CH$_3$)CH$_2$CH$_3$;

$R^9$=isopropyl, trifluormethyl, chlormethyl, isobutyl, ethyl, cyclopropyl, CH$_2$-cyclopropyl, CH(CH$_3$)CH$_2$CH$_3$, cyclopentyl, cyclohexyl;

$R^{17}$=methyl, ethyl, propyl, isopropyl, butyl, isobutyl, CH=C(CH$_3$), cyclopropyl, cyclobutyl, cyclohexyl;

$R^{20}$=methyl, ethyl, propyl, isopropyl, phenyl;

$R^{19}$=

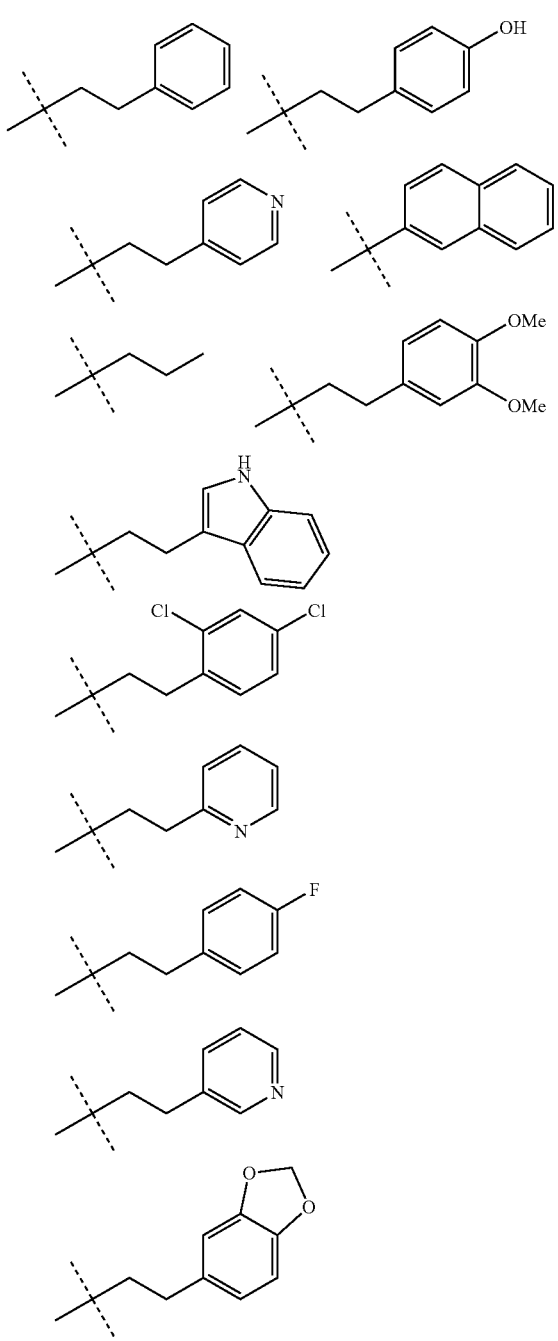

-continued

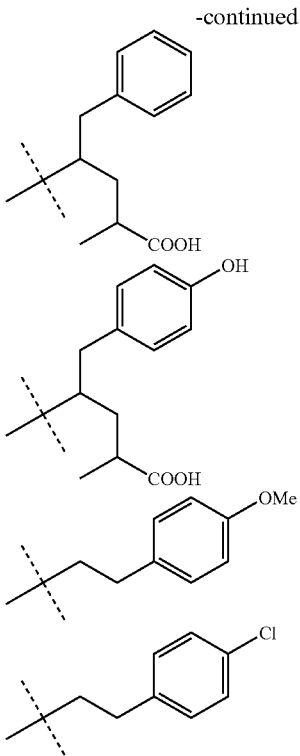

The invention claimed is:

1. A compound of the following general formula:

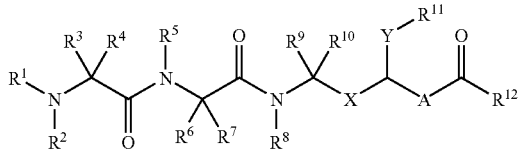

wherein:
A represents an optionally substituted 5- or 6-membered heteroaryl ring
X is O, S or a group of Formula $NR^{13}$ or $CR^{14}R^{15}$;
Y is O, S or a group of Formula $NR^{16}$ and
$R^1$, $R^4$, $R^5$, $R^6$, $R^7$, $R^9$, $R^{10}$, $R^{11}$, $R^{13}$, $R^{14}$, $R^{15}$ and $R^{16}$ are independently of each other H, alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl,
$R^2$ and $R^3$ together constitute a group of Formula $(CH_2)n$ wherein n is 4; and
$R^8$ is hydrogen or alkyl;
$R^{12}$ is H, alkyl, alkenyl, alkynyl, heteroalkyl, aryl, heteroaryl, cycloalkyl, alkylcycloalkyl, heteroalkylcycloalkyl, heterocycloalkyl, aralkyl, heteroaralkyl or $NR^{18}R^{19}$;
$R^{18}$ is H or methyl; and
$R^{19}$ is aralkyl or heteroaralkyl
or a pharmacologically acceptable salt, solvate, hydrate or a pharmacologically acceptable formulation thereof.

2. A compound of claim 1, wherein A has the following structure:

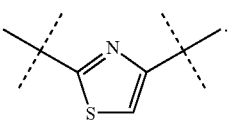

3. The compound according to claim 1 wherein $R^{12}$ is $NR^{18}R^{19}$;
$R^{18}$ is H or methyl;
$R^{19}$ has the formula:

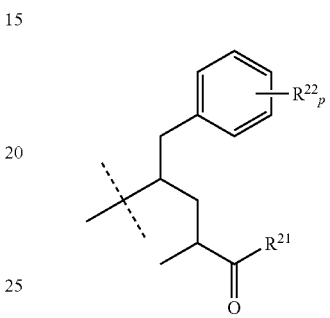

wherein:
$R^{21}$ is —OH, —$NH_2$, alkyloxy, alkylamino or dialkylamino;
$R^{22}$ is halogen, —OH, —$NO_2$, —$NH_2$, alkyloxy, alkylamino or dialkylamino; and
p is 0, 1, 2 or 3.

4. A compound of claim 1 wherein X is a $CH_2$ group.
5. A compound of claim 1 wherein Y is O.
6. A compound of claim 1 wherein $R^1$ is $C_1$-$C_4$ alkyl.
7. A compound of claim 1 wherein $R^4$ is H or methyl.
8. A compound of claim 1 wherein $R^5$ is H.
9. A compound of claim 1 wherein $R^6$ is $C_1$-$C_6$ alkyl, $C_3$-$C_6$ cycloalkyl or $C_4$-$C_7$ alkylcycloalkyl.
10. A compound of claim 1 wherein $R^7$ is H or methyl.
11. A compound of claim 1 wherein $R^9$ is $C_1$-$C_6$ alkyl.
12. A compound of claim 1 wherein $R^{10}$ is H or methyl.
13. A compound of claim 1 wherein $R^{11}$ is H or a group of Formula (C=O)—($C_{1-4}$)alkyl.
14. A compound of claim 1 wherein $R^{12}$ is a group of Formula $NR^{18}R^{19}$, wherein $R^{18}$ is H or methyl and $R^{19}$ is aralkyl or heteroaralkyl.
15. A pharmaceutical composition comprising a compound of claim 1 and optionally one or more carriers and/or adjuvants.
16. A method for treating a patient suffering from colon adenocarcinoma, breast adenocarcinoma, ovarian adenocarcinoma, epidermoid adenocarcinoma or prostate adenocarcinoma, comprising administering to the patient one or more compounds of claim 1.
17. The method of claim 16 wherein the patient is identified as suffering from colon adenocarcinoma, breast adenocarcinoma, ovarian adenocarcinoma, epidermoid adenocarcinoma or prostate adenocarcinoma, and the one or more compounds are administered to the identified patient.

* * * * *